US007749540B2

(12) United States Patent
Jacobs et al.

(10) Patent No.: US 7,749,540 B2
(45) Date of Patent: *Jul. 6, 2010

(54) COMPOSITIONS COMPRISING MODAFINIL COMPOUNDS

(75) Inventors: Martin J. Jacobs, West Chester, PA (US); Bradley T. McIntyre, Thorndale, PA (US); Piyush R. Patel, Wallingford, PA (US); David A. Dickason, Cincinnati, OH (US)

(73) Assignee: Cephalon, Inc., Frazer, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/975,350

(22) Filed: Oct. 11, 2001

(65) Prior Publication Data

US 2002/0098240 A1 Jul. 25, 2002

Related U.S. Application Data

(60) Provisional application No. 60/239,490, filed on Oct. 11, 2000.

(51) Int. Cl.
*A61K 9/14* (2006.01)
*A61K 31/165* (2006.01)

(52) U.S. Cl. .................................. 424/488; 514/618

(58) Field of Classification Search ................. 424/489, 424/451, 452, 455, 498, 464; 514/618, 923, 514/937

See application file for complete search history.

(56) References Cited

U.S. PATENT DOCUMENTS

| | | | |
|---|---|---|---|
| 4,151,143 A | | 4/1979 | Blank et al. |
| 4,177,290 A | | 12/1979 | Lafon |
| 4,927,855 A | * | 5/1990 | Lafon ..................... 514/618 |
| 5,180,745 A | * | 1/1993 | Lafon ..................... 514/618 |
| 5,422,384 A | | 6/1995 | Samuels et al. |
| 5,510,119 A | * | 4/1996 | Santus et al. ............ 424/490 |
| 5,589,485 A | * | 12/1996 | Hochlowski et al. ..... 514/315 |
| 5,618,845 A | * | 4/1997 | Grebow et al. .......... 514/618 |
| 5,843,347 A | * | 12/1998 | Nguyen et al. ............. 264/9 |
| 6,200,968 B1 | | 3/2001 | Dickason et al. |
| 6,264,981 B1 | | 7/2001 | Zhang et al. |
| RE37,516 E | | 1/2002 | Grebow et al. |
| 6,348,500 B1 | * | 2/2002 | Fu ........................... 514/618 |
| 6,489,363 B2 | * | 12/2002 | Jacobs et al. ............ 514/615 |
| 6,566,404 B2 | * | 5/2003 | Esteve et al. ............ 514/618 |

FOREIGN PATENT DOCUMENTS

| | | |
|---|---|---|
| WO | WO 92/21348 | 12/1992 |
| WO | WO 94/21371 | 9/1994 |
| WO | WO 99/25329 | 5/1999 |
| WO | WO02/10125 | 2/2002 |

OTHER PUBLICATIONS

Shah et al. ("Self-emulsifying drug delivery systems (SEDDS) with polyglycolized glycerides for improving in vitro dissolution and oral absorption of lipophilic drugs," in international Journal of Pharmaceutics, 106 (1994), pp. 15-23).*
Charman et al. ("Self-emulsifying Drug Delivery Systems: Formulation and Pharmaceutical Evaluation of an Investigational Lipophilic Compound," in Pharmaceutical Research, vol. 9, No. 1, 1992, pp. 87-93).*
Shah et al. ("Self-emulsifying drug delivery systems (SEDDS) with polyglycolized glycerides for improving in vitro dissolution and oral absorption of lipophilic drugs," in international Journal of Pharmaceutics, 106 (1994), pp. 15-23).*
Charman et al. ("Self-emulsifying Drug Delivery Systems: Formulation and Pharmaceutical Evaluation of an Investigational Lipophilic Compound," in Pharmaceutical Research, vol. 9, No. 1, 1992, pp. 87-93).*
Rambert, F.A. et al., *Neuropschychopharmacology*, 1994, 10(3S), 169S.
Charman, S.A. et al., *Pharmaceutical Research*, 1992, 9(1), 87-93.
Hauss, D.J. et al., *Journal of Pharmaceutical Sciences*, 1998, 87(2), 164-169.
Jonkman-De Vries, J.D. et al., *PDA Journal of Pharmaceutical Science & Technology*, 1995, 49(6), 283-288.
Shah, N.H. et al., *International Journal of Pharmaceutics*, 1994, 106, 15-23.
Emulsions. *Kirk-Othmer Encyclopedia of Chemical Technology*, 3d ed.; Wiley & Sons: New York, 1979; vol. 8, pp. 900-930.
Sertsou, G. et al., "Factors affecting incorporation of drug into solid solution with HPMCP during solvent change co-precipitation," *Int. J. Pharmaceutics*, 2002, 245, 99-108.

\* cited by examiner

*Primary Examiner*—Blessing M Fubara

(57) ABSTRACT

Particle-forming compositions of modafinil compounds, and aqueous compositions of particles, wherein the particles comprise a modafinil compound, are disclosed, along with methods of their preparation, and their use in the treatment of diseases.

45 Claims, No Drawings

COMPOSITIONS COMPRISING MODAFINIL COMPOUNDS

This Application claims benefit of U.S. provisional Application Ser. No. 60/239,490 filed Oct. 11, 2000.

FIELD OF THE INVENTION

The invention relates to particle-forming compositions comprising a modafinil compound. The invention is also directed to compositions of suspended particles which are formed when the particle-forming compositions are contacted with an aqueous medium. The invention is further directed to methods of preparation of the compositions, and the use of the compositions in the treatment of diseases to a subject in need thereof.

BACKGROUND OF THE INVENTION

Modafinil ($C_{15}H_{15}NO_2S$), is 2-(benzhydryl-sulfinyl)acetamide, and is also known as 2-[(diphenylmethyl) sulfinyl] acetamide.

Modafinil has been described as presenting a "neuropsychopharmacological spectrum characterized by the presence of excitation with hyperactivity and of hypermotility; and by the absence of stereotypy (except in high doses) and of potentialization of the effects of apomorphine and amphetamine" (U.S. Pat. No. 4,177,290; hereinafter the "'290 patent," which is incorporated in its entirety herein by reference). A single administration of modafinil results in increased locomotor activity in mice and increased nocturnal activity in monkeys (Duteil et al., Eur. J. Pharmacol. 180:49 (1990)). Modafinil has been successfully tested in humans for treatment of idiopathic hypersomnia and narcolepsy (Bastuji et al., Prog. Neuro-Psych. Biol. Psych. 12:695 (1988)).

Other uses of modafinil have been presented. U.S. Pat. No. 5,180,745, incorporated in its entirety herein by reference, discloses the use of modafinil for providing a neuroprotective effect in humans, and in particular for the treatment of Parkinson's disease. The levorotatory form of modafinil, i.e., (-)benzhydrylsulfinyl-acetamide, may have potential benefit for treatment of depression, hypersomnia and Alzheimer's disease (U.S. Pat. No. 4,927,855, incorporated in its entirety herein by reference). European Published Application 547952 (published Jun. 23, 1993) discloses the use of modafinil as an anti-ischemic agent. European Published Application 594507 (published Apr. 27, 1994) discloses the use of modafinil to treat urinary incontinence.

Preparations of modafinil having a defined solid particle size have been described in U.S. Pat. No. 5,618,845, incorporated in its entirety herein by reference, and preparations of a levorotatory isomer of modafinil was described in U.S. Pat. No. 4,927,855. Heterocyclic derivatives of modafinil are disclosed in U.S. Patent Application No. 60/204,789, incorporated in its entirety herein by reference.

Modafinil has been approved for use in humans in 100 mg and 200 mg solid unit dose forms in the U.S. It is also desirable to formulate modafinil in liquid compositions. It has been observed that modafinil has very poor water and lipid solubility and it is therefore difficult to solubilize modafinil in pharmaceutically-acceptable compositions. Conventional solid and liquid formulations that include modafinil are described in the '290 patent. Liquid suspensions or emulsions of modafinil were mentioned in U.S. Pat. No. 5,618,845. A suspension of modafinil was reported in U.S. Pat. No. 5,180,745. An aqueous cyclodextrin solution of modafinil was described in Rambert, F. A., et al. *Neuropsychopharmacology*, 10(3S), Part 2 (May 1994).

A technique recently developed to formulate liquid pharmaceutical compositions for agents that display very low water solubility involves a self-emulsifying drug delivery system, known as "SEDDS". These drug delivery systems are isotropic mixtures of lipids or lipid-soluble compounds and a surfactant that rapidly form thermodynamically stable microparticles upon contact with water. See, e.g., Shah et al., *International Journal of Pharmaceutics (Netherlands)*, 106:15-23, (1994), which is incorporated in its entirety herein by reference.

Despite the low lipid solubility of modafinil, it has been discovered that modafinil can be formulated to produce particle-forming compositions, wherein the compositions are capable of forming particles comprising a modafinil compound upon contact with water. These compositions have been found to effectively solubilize modafinil in an aqueous component and to provide for effective bioavailable delivery of modafinil to a subject in need thereof.

SUMMARY OF THE INVENTION

Accordingly, one object of the present invention is to provide particle-forming compositions comprising a modafinil compound. Particularly, the particle-forming compositions of the present invention are non-aqueous and optionally comprise an amount of at least one surfactant sufficient to allow for the formation of a composition of particles upon contact of the particle-forming composition with an aqueous medium.

It is another object of the invention to provide for compositions of particles in an aqueous medium, wherein the particles comprise a modafinil compound.

Preferably the compositions of particles comprises a stable suspension, wherein the suspended particles comprise a modafinil compound.

Preferably, both the particle-forming compositions and the compositions of particles, wherein the particles comprise a modafinil compound, are pharmaceutically acceptable compositions and allow for bioavailable delivery of a modafinil compound upon oral administration to a subject in need thereof.

It is another object of the invention to provide a method of forming a composition of particles in an aqueous medium which comprises contacting the particle-forming compositions comprising a modafinil compound with an aqueous medium.

It is another object of the invention to provide a method of treating a disease or disorder in a subject which comprises administering to the subject a therapeutically effective amount of either of the compositions of the present invention.

These and other objects, which will become apparent during the following detailed description, have been achieved by the inventors' discovery that despite its poor aqueous and lipid solubility, a modafinil compound can be formulated to provide effective bioavailability upon administration to a subject in need thereof.

DETAILED DESCRIPTION OF THE INVENTION

Thus, in a first embodiment, the present invention provides a particle-forming composition comprising a modafinil compound. Preferably the particle-forming composition is non-aqueous. Preferably the particle-forming composition comprises at least one surfactant. Preferably the particle-forming composition comprises modafinil.

In a second embodiment, the present invention provides for a composition of particles in an aqueous medium, wherein the particles comprise a modafinil compound. Preferably the composition of particles comprises at least one surfactant. Preferably the particles comprise modafinil. Preferably the composition of particles is a stable suspension.

In certain preferred embodiments, the compositions are pharmaceutically acceptable.

As used herein, "the compositions" refers collectively to the particle-forming compositions and the compositions of particles wherein the particles comprise a modafinil compound.

As used herein, a "non-aqueous" composition refers to a composition that contains from 0-10% water by weight.

As used herein, "aqueous medium" refers to any medium comprised of greater than 10% water.

As used herein, a "particle-forming composition" refers to a composition that is capable of forming particles upon contact with an aqueous medium. Preferably the particle-forming composition is a liquid or solid solution.

As used herein, "particle" or "particles" refers to substantially non-crystalline structures, preferably an aggregation of molecules in a discrete non-crystalline structure, such as a micelle, microsphere, droplet, colloid, or globule. Preferably the particles comprise a modafinil compound, and more preferably, comprise modafinil.

As used herein, "composition of particles" refers to a composition comprising a particle wherein the particle comprises a modafinil compound.

As used herein, "stable suspension" refers to a mixture of particles that remain intact and dispersed in a liquid medium such that the suspension can be stored and administered in a pharmaceutically acceptable manner.

As used herein, "a modafinil compound" or "modafinil compound" and the like, refers to modafinil, its racemic mixtures, individual isomers, acid addition salts, such as a metabolic acid of modafinil, benzhydrylsulfinylacetic acids, and its sulfone forms, hydroxylated forms, polymorphic forms, analogs, derivatives, cogeners and prodrugs thereof. Prodrugs are known in the art as compounds that are converted to the active agent (a modafinil compound) in the body of a subject. In certain preferred embodiments, the modafinil compound is modafinil.

As used herein, "bioavailable" is intended to mean a portion of the administered dose that is absorbed in the blood stream and can readily be determined by techniques known in the art, such as, for example, by measuring the blood serum level of a compound.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, the term "subject" refers to a warm blooded animal such as a mammal, preferably a human or a human child, which is afflicted with, or has the potential to be afflicted with one or more diseases and conditions described herein.

As used herein, "therapeutically effective amount" refers to an amount which is effective in reducing, eliminating, treating, preventing or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, "unit dose" means a single dose which is capable of being administered to a subject, and which can be readily handled and packaged, remaining as a physically and chemically stable unit dose comprising either a modafinil compound, or a pharmaceutically acceptable composition comprising a modafinil compound.

As used herein, a "lower alkyl alcohol" refers to a branched or straight-chained alkyl alcohol containing from 1 to 6 carbon atoms, such as methanol, ethanol, n-propanol, isopropanol, n-butanol, isobutyl alcohol, sec-butyl alcohol, t-butyl alcohol, pentanol, hexanol, etc; with preferred lower alkyl alcohols including ethanol, propanol and isopropanol.

As used herein, the term "arylalkyl alcohol" refers to aryl-substituted $C_1$-$C_6$ alkyl alcohols such as benzyl alcohol, phenethyl alcohol, diphenylmethyl alcohol (benzhydrol), etc.; with preferred arylalkyl alcohols including benzyl alcohol, α-phenethyl alcohol and β-phenethyl alcohol.

As used herein, "antioxidant" is intended to indicate any substance useful to retard deterioration by oxidation or to inhibit reactions promoted by oxygen or peroxides.

As used herein, "lipid" is intended to indicate a fat, oil, wax, sterol, glycerol ether, triglyceride, or combination thereof.

As used herein, the term "about" refers to a range of values ±10% of a specified value. For example, the phrase "about 50%" includes ±10% of 50, or from 45 to 55%.

In certain preferred embodiments, the compositions comprise a modafinil compound at a concentration of about 1 to about 500 mg/ml. In certain more preferred embodiments, a modafinil compound is present from about 1 to about 200 mg/ml, and most preferably from about 20 to about 80 mg/ml.

In certain embodiments, the compositions comprise at least one surfactant. In other preferred embodiments, there are three surfactants, and other more preferred embodiments include one or two surfactants. In certain embodiments, the surfactant acts as the primary solubilizing agent. In other embodiments, the compositions comprise from about 0.5% to about 50% total surfactant. The amount of total surfactant is more preferably at least 5%, and less than about 40%, depending upon the surfactant and the additional components of the composition. Preferably, appropriate surfactants are those, when admixed with a modafinil compound, result in particle-forming compositions and compositions of particles, and more preferably, in stable suspensions. One skilled in the art can readily determine the appropriate surfactant or combination of surfactants, and their relative amounts, by use of conventional techniques and observing the characteristics of the resultant composition. Several factors can be considered, including for example, the solubility of the modafinil compound in the solution, the degree of precipitation of the modafinil compound, the degree of solubilization or emulsification of the solution and the stability of the solution over a period of time.

The surfactants include, but are not limited to, polyoxyethylene sorbitan fatty acid esters, polyethylene glycol ethers, saturated polyglycolized glycerides, fatty acid esters of polyethylene glycols, medium chain monoglycerides, medium chain fatty acid esters, d-α-tocopheryl polyethylene glycol succinate, polyethylene/propylene glycol copolymers, block copolymers of ethylene oxide and propylene oxide, polyoxyl stearates, ethoxylated castor oils, and ethoxylated hydroxystearic acids. Additional surfactants can be found in *The Handbook of Pharmaceutical Excipients, 2nd Ed.*, (The Pharmaceutical Press, London and American Pharmaceutical Association (1994)), a common text in the field, which is hereby incorporated by reference in its entirety.

The polyoxyethylene sorbitan fatty acid esters (polysorbates) are non-ionic surfactants (detergents) that may comprise a mixture of fatty acids. Commercially available examples are polyoxyethylene (20) sorbitan monolaurate (such as Tween® 20), polyoxyethylene (40) sorbitan monopalmitate (such as Tween® 40), polyoxyethylene (80) sorbitan monooleate (such as Tween® 80) and sorbitan monolaurate (such as Span® 20). Preferred polyoxyethylene sorbitan fatty acid esters are polyoxyethylene (80) sorbitan monooleate (in particular, Tween® 80) and sorbitan monolaurate (in particular, Span® 20). The saturated polyglycolized glycerides include, for example, mono-, di-, or triglycerides. The di-fatty acid esters of polyethylene glycols include, for example, Gelucire® 44/14 (primarily a fatty acid ester of PEG-1500, available from Gattefossé, Saint-Priest, France). The medium chain monoglycerides, wherein the chain length is from 6 to 10 carbon atoms, include for example, glyceryl monocaprylate (Imwitor® 308), glyceryl monocaproate (Capmul® MCM C-8), glyceryl caprylate/caprate (Capmul® MCM) and a mixture of polyoxyethylene glyceryl caprylate and polyoxyethylene glyceryl caproate (Labrasol®). The medium chain fatty acid esters include medium chain length triglycerides, such as a mixture of glyceryl tricaprate and glyceryl tricaprilate (Miglyol® 612). The block copolymers of ethylene oxide and propylene oxide include, for example, polyoxyethylene-polyoxypropylene block co-polymer (Pluronic® F-68). The polyoxyl stearates include polyethoxylated (40) stearic acid (Myrj® 52). The ethoxylated castor oils include, for example, polyethoxylated (60) hydrogenated castor oil (Cremophor® EL). The ethoxylated hydroxystearic acids include, for example, polyethylene glycol 660 hydroxystearate (Solutol® HS 15). Some surfactants are solid or semisolid at room temperature, e.g., glyceryl monocaprylate, and Gelucire® 44/14.

Examples of surfactants which are particularly effective as the primary solubilizing agent, such as those compositions where the surfactant comprises more than 50% of the composition, include polyethoxylated (60) hydrogenated castor oil (such as Cremophor® EL), polyethylene glycol 660 hydroxystearate (such as Solutol® HS 15), polyethoxylated (40) stearic acid (such as Myrj® 52) and polyoxyethylene (80) sorbitan monooleate (such as Tween® 80).

In other preferred embodiments, the compositions comprise more than one surfactant. In certain embodiments, the additional surfactants may be selected from any of the aforementioned surfactants. Preferably, an additional, or second surfactant, is a polyoxyethylene sorbitan fatty acid ester, and more preferably is polyoxyethylene (80) sorbitan monooleate (in particular, Tween® 80) and sorbitan monolaurate (in particular, Span® 20).

In other embodiments, the compositions comprise a polyoxyethylene sorbitan fatty acid ester, preferably polyoxyethylene (80) sorbitan monooleate (in particular, Tween® 80); medium chain monoglycerides, in particular, glyceryl caprylate/caprate (Capmul® MCM); and medium chain length triglycerides, such as a mixture of 20 glyceryl tricaprate and glyceryl tricaprilate (in particular, Miglyol® 612). A preferred composition comprises Tween® 80, Capmul® MCM, and Miglyol® 612.

In certain embodiments of the invention, the compositions comprise at least one organic solvent. In certain preferred embodiments, there are three solvents, and other more preferred embodiments include one or two solvents. In certain preferred embodiments, the amounts of any additional solvents comprise from about 0.5% to about 50% (v/v) of the composition, with a more preferred amount of about 1% to about 50% (v/v), and a most preferred amount about 5% to about 20% (v/v).

Preferably, an appropriate organic solvent is one which increases the solubility of a modafinil compound in a particle-forming composition and does not adversely impact upon the formation of suspended particles.

In certain preferred embodiments, the compositions comprise at least one organic solvent including glycerin, propylene glycol, diethylene glycol ethyl ether, propylene carbonate, tetraglycol (also known as glycofurol), medium chain length monoglycerides, or polyethyleneglycols. Medium chain length monoglycerides include glyceryl monocaprylate (Imwitor®), glyceryl caprylate/caprate (such as Capmul®) and polyoxyethylene glyceryl caproate (such as Labrasol®). Preferred organic solvents include polyethylene glycols or "PEG", which refer to a liquid or solid polymer of the general formula $H(OCH_2CH_2)_nOH$, wherein n is at least 4. The preferred PEG has an average molecular weight of from about 200 to about 1500, and commercially available PEG materials include PEG-200, PEG-300, PEG-400, PEG-540, PEG-600, PEG-800, PEG-1000 and PEG-1450. All are commercially available from, for example, from Union Carbide Corporation in both food or pharmaceutical grades. Preferred PEG solvents for use in the present composition include PEG-300, PEG-400 and PEG 1450, with PEG-300 and PEG-400 being more preferred.

In certain embodiments, the compositions comprise glycol and a surfactant. Preferably the surfactant is an ethoxylated hydroxystearic acid, and in particular is polyethylene glycol 660 hydroxystearate. In certain preferred embodiments, the ratio of glycol to surfactant is 1:1.

In other preferred embodiments, the compositions comprise an additional, or second solvent, which is preferably a lower alkyl alcohol or an alkylaryl alcohol, and more preferably benzyl alcohol, α-phenethyl alcohol or β-phenethyl alcohol. In more preferred embodiments, the solvent system includes mixtures of a polyethylene glycol and an arylalkyl alcohol. More preferred embodiments include mixtures of PEG-400 and benzyl alcohol, PEG-400 and α-phenethyl alcohol, and PEG-400 and β-phenethyl alcohol. A most preferred embodiment includes a mixture of 95:5 (v/v) PEG-400:benzyl alcohol.

In certain preferred embodiments, the compositions comprise a modafinil compound, or preferably modafinil, at a concentration of about 1 to about 100 mg/ml, preferably from about 1 to about 60 mg/ml and more preferably from about 20 to about 50 mg/ml; a first surfactant selected from a polyoxyethylene sorbitan fatty acid ester, a polyethylene glycol ether, a saturated polyglycolized glyceride, a fatty acid ester of a polyethylene glycol, a medium chain monoglyceride, a medium chain fatty acid ester, d-α-tocopheryl polyethylene glycol succinate, a polyethylene/propylene glycol copolymer, block copolymers of ethylene oxide and propylene oxide, a polyoxyl stearate, an ethoxylated castor oil, and an ethoxylated hydroxystearic acid; and may additionally comprise a second surfactant selected from a polyoxyethylene sorbitan fatty acid ester; and may further additionally comprise an organic solvent selected from glycerin, propylene glycol, diethylene glycol ethyl ether, propylene carbonate, a medium chain length monoglyceride, and a polyethyleneglycol. In a more preferred embodiment, the compositions are pharmaceutically acceptable.

In certain further preferred embodiments, the first surfactant is a saturated polyglycolized glyceride, a fatty acid ester of a polyethylene glycol, or a medium chain monoglyceride; the second surfactant is a polyoxyethylene sorbitan fatty acid ester; and the organic solvent is a polyethyleneglycol. In more preferred embodiments, the first surfactant is glyceryl caprylate/caprate, glyceryl monocaprylate or polyethoxylated (40) stearic acid; the second surfactant is sorbitan monolaurate; and the organic solvent is PEG-300 or PEG-400.

In certain most preferred embodiments, the compositions comprise 90% PEG-400, 5% sorbitan monolaurate, 5% glyceryl caprylate/caprate (w/w/w), or in particular, 90% PEG-400, 5% Span® 20, 5% Capmul® MCM (w/w/w). In other most preferred embodiments, the compositions comprise 90% PEG-400, 5% sorbitan monolaurate, 5% glyceryl monocaprylate (w/w/w), or in particular, 90% PEG-400, 5% Span® 20, 5% Imwitor® 308 (w/w/w). In another most preferred embodiment, the compositions comprise 90% PEG-400, 5% sorbitan monolaurate, 5% polyethoxylated (40) stearic acid (w/w/w), or in particular, 90% PEG-400, 5% Span® 20, 5% Myrj® 52 (w/w/w).

In other more preferred embodiments, the first surfactant is glyceryl caprylate/caprate, glyceryl monocaprylate, polyethoxylated (40) stearic acid or a mixture of polyoxyethylene glyceryl caprylate and polyoxyethylene glyceryl caproate; the second surfactant is polyoxyethylene (80) sorbitan monooleate; and the organic solvent is PEG-300 or PEG-400.

In other most preferred embodiments, the compositions comprise 70% PEG-400, 15% polyoxyethylene (80) sorbitan monooleate, 15% glyceryl caprylate/caprate (w/w/w), in particular, 70% PEG-400, 15% Tween® 80, 15% Capmul® MCM (w/w/w). In another most preferred embodiment, the compositions comprise 70% PEG-400, 15% polyoxyethylene (80) sorbitan monooleate, 15% glyceryl monocaprylate (w/w/w), in particular, 70% PEG-400, 15% Tween® 80, 15% Imwitor® 308 (w/w/w). In a further most preferred embodiment, the compositions comprise 70% PEG-400, 15% polyoxyethylene (80) sorbitan monooleate, 15% polyethoxylated (40) stearic acid (w/w/w), in particular, 70% PEG-400, 15% Tween® 80, 15% Myrj® 52 (w/w/w). In an additional most preferred embodiment, the compositions comprise 70% PEG-400, 15% polyoxyethylene (80) sorbitan monooleate, 15% of a mixture of polyoxyethylene glyceryl caprylate and polyoxyethylene glyceryl caproate (w/w/w), in particular, 70% PEG-400, 15% Tween® 80, 15% Labrasol® (w/w/w).

In another embodiment, the present invention provides for a method of preparing a composition of particles, wherein the particles comprise a modafinil compound, comprising contacting a particle-forming composition of a modafinil compound with an aqueous medium. Preferably, the modafinil compound is modafinil.

In yet another embodiment, the present invention provides a method of preparing a composition of particles, wherein the particles comprise a modafinil compound, comprising:
(a) dissolving a modafinil compound in a liquid comprising at least one surfactant to form the particle-forming composition; and
(b) contacting the particle-forming composition with an aqueous medium to form a composition of particles. In a preferred embodiment, the amount of surfactant is from about 1% to about 50% by weight of the composition. In a preferred embodiment, the modafinil compound is modafinil. In another preferred embodiment, the composition of particles is formed by contacting the particle-forming composition with the aqueous medium in vitro. In yet another preferred embodiment, the composition of particles is formed by contacting the particle-forming composition with the aqueous medium in vivo.

In a further embodiment of the present invention, there is provided a method of treating a disease or disorder in a subject, comprising administering a therapeutically effective amount of a modafinil compound, or preferably modafinil in a particle-forming composition comprising at least one surfactant to the subject. In a preferred embodiment, the particle-forming composition contacts with aqueous medium in vivo, thereby forming a composition which is therapeutically effective.

In yet another embodiment, the present invention provides for a method of treating a disease or disorder in a subject, comprising:
(a) contacting a modafinil compound in a particle-forming composition comprising at least one surfactant with an aqueous medium, thereby forming a composition of particles, wherein the particles comprise a modafinil compound; and
(b) administering a therapeutically effective amount of the composition of particles to a subject. In a preferred embodiment, the modafinil compound is modafinil.

In another embodiment, the present invention provides for the use of a modafinil compound, or preferably modafinil for the preparation of pharmaceutical compositions useful in the treatment of a disease or disorder.

In certain preferred embodiments, the pharmaceutical compositions are useful for treatment of sleepiness, such as excessive daytime sleepiness associated with narcolepsy, or sleepiness associated with sleep apneas, tiredness, Parkinson's disease, cerebral ischemia, stroke, sleep apneas, eating disorders, attention deficit hyperactivity disorder, cognitive dysfunction or fatigue, such as fatigue resulting from multiple sclerosis ("MS fatigue"); and for promotion of wakefulness, stimulation of appetite, or stimulation of weight gain.

In certain embodiments, administration of a therapeutically effective amount of the composition can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

A therapeutically effective amount of a modafinil compound will vary depending upon a number of factors, including the dosage of the drug to be administered, the chemical characteristics (e.g., hydrophobicity) of the compounds employed, the potency of the compounds, the type of disease, the diseased state of the patient, and the route of administration. Generally, treatment is initiated with small dosages, which can then be increased by small increments until the optimum desired effect under the circumstances is achieved.

In certain preferred embodiments, the compositions comprise at least one unit dose of a modafinil compound. In certain more preferred embodiments, the compositions comprise one unit dose of modafinil. Preferable daily doses of modafinil range from about 0.01 to 100 mg/kg of body weight. By way of general guidance, daily doses for humans range from about 0.1 mg to about 2000 mg. Preferably the unit dose range is from about 1 to about 500 mg administered one to four times a day, and even more preferably from about 10 mg to about 400 mg, one to two times a day. In certain preferred embodiments, the unit dose is 100 or 200 mg. In other preferred embodiments, a unit dose is one that is necessary to achieve a blood serum level of about 0.05 to 30 µg/ml, and more preferably, of about 1 to about 20 µg/ml in a subject.

In a further embodiment, the present invention provides for the compositions comprising a modafinil compound and at least one surfactant, wherein upon administration of either of the compositions to a subject, the modafinil compound has a blood serum level of about 0.05 to about 30 µg/ml in said subject. In a preferred embodiment, the modafinil compound has a blood serum level of about 1 to about 20 µg/ml in said subject. In another preferred embodiment, the composition being administered to achieve the desired blood serum levels is a particle-forming composition comprising a modafinil compound. In a further preferred embodiment, the composition being administered to achieve the desired blood serum levels is an aqueous composition of particles, wherein the particles comprise a modafinil compound. In more preferred embodiments, the modafinil compound is modafinil.

In a further embodiment, the present invention provides for compositions that are suitable for oral administration to a subject. Oral administration includes ingestion in the form of a liquid composition, such as a syrup, elixir, emulsion; or a capsule. A preferred embodiment is in the form of a capsule, and more preferably as hard capsules, comprising gelatin, hydroxypropylmethylcellulose ("cellulose"), or starch. Another more preferred embodiment is in the form of soft gelatin capsules. In particular, the soft gel capsules comprise a non-aqueous composition. In additional preferred embodiments, the composition being used for oral administration is a particle-forming composition comprising a modafinil compound. In further preferred embodiment, the composition being used for oral administration is an aqueous composition of particles, wherein the particles comprise a modafinil compound.

In other embodiments of the invention, the compositions may also be prepared in admixture with additional pharmaceutically-acceptable excipients or components to further promote effective therapeutic use. The excipients may include lipids, for example, those which are useful to change particle size; antibacterial agents such as benzyl alcohol or methyl paraben; antioxidants such as ascorbic acid, sodium bisulfite, and fatty acid esters of ascorbic acid, such as ascorbyl palmitate; chelating agents such as ethylene diaminetetraacetic acid; buffers such as acetates, citrates or phosphates and agents for the adjustment of toxicity such as sodium chloride or dextrose; and other excipients such as flavorings, sweetening agents and coloring agents. Other appropriate excipients can readily be determined by one skilled in the art, and may further include those found in *The Handbook of Pharmaceutical Excipients, 2nd Ed.*, (The Pharmaceutical Press, London and American Pharmaceutical Association (1994)).

The compositions of the present invention comprise modafinil compounds, which may be readily prepared by one skilled in the art using conventional methods.

Methods for preparing modafinil and various derivatives appear in U.S. Pat. No. 4,177,290, and methods for preparing other modafinil compounds appear in U.S. Pat. Nos. 4,927,855, 5,719,168 and in U.S. patent application No. 60/204,789.

There is wide latitude in formulation of the compositions of the present invention. The compositions of particles may be formed by contacting the particle-forming compositions comprising a modafinil compound with an aqueous medium in vitro, i.e., subjected to predilution, prior to ingestion by the subject, or in vivo, e.g. contact with aqueous contents of the gastrointestinal composition of the subject. If the composition is prediluted, a preferable dilution ratio is from about 1:1000 (1 part formulation to 999 parts aqueous medium) to about 1:2 (1 part formulation to 1 part aqueous medium). More preferably, the dilution ratio is from about 1:500 (1 part formulation to 499 parts aqueous medium) to about 1:3 (1 part formulation to 2 parts aqueous medium). By way of general guidance, for administration to humans a convenient ratio is about 1:250, which is a rough correspondence to a 1 ml unit dose dispersed in an 8-ounce glass of an aqueous liquid.

In certain preferred embodiments, when the particle-forming composition is contacted with an aqueous medium, a homogeneous, stable composition comprising suspended particles is formed. Preferably, the particles comprise a modafinil compound. Typically, the particles are thermodynamically stable, and are formed spontaneously upon mixing, without external mechanical agitation. The particles are preferably in the microparticle size range, with a diameter of about 1 to about 1000 nm. More preferably, the particles have a diameter of about 1 to about 400 nm, and most preferably about 1 to about 100 nm.

A feature of these preferred compositions is that they are translucent and optically isotropic. A useful indication of the particle size is the degree of optical transparency of a given volume of water comprising a given amount of formulation. This is due to the scattering of visible light by the particles, with the larger particles causing greater scattering. In general, the greater the optical transparency, the smaller the particle size. High optical transparency, i.e., bluish haze invisible or nearly invisible, generally indicates a particle size of less than 100 nm. A distinct bluish haze generally indicates a particle size from about 100 nm to about 400 nm. Without intending to be bound by theory, it is noted that particle size tends to be essentially constant for a given formulation, regardless of the dilution ratio. If particles fail to form, an increase in dilution ratio, or an adjustment of the amount and type of surfactant may be used to promote particle formation.

An additional feature of these preferred compositions is that they remain physically stable, which allows for desirable and effective use of the compositions as pharmaceutically acceptable formulations. An indication of a stable compositions is retention of the same outward appearance and properties over an extended period of time, sufficient to retain pharmaceutical acceptability. In stable compositions, the particles generally remain intact and sufficiently dispersed or suspended in the liquid medium. Typically, creaming or sedimentation is minimal, or otherwise, the particles can be redispersed upon mild agitation. Additionally, the particles do not readily or irreversibly aggregate, coalesce, or otherwise revert back to two separate bulk phases.

The compositions of the present invention may be a liquid, semi-solid, or solid at room temperature. If liquid, the compositions may be contained in a capsule. If semi-solid or solid, the compositions can be in the form of a capsule or tablet.

Whether a composition according to the invention is a liquid, semi-solid, or solid at room temperature, may depend upon the selection of components, or other concerns such as commercial viability, administration and the like. For example, a semi-solid or solid formulation is convenient for manufacturing unit doses of modafinil compound in the form of a capsule, including both hard gelatin and soft gelatin capsules, and tablets. When the liquid or solid formulation contacts an aqueous medium, e.g., gastrointestinal liquids, the formulation disperses into suspended particles in which modafinil compound is biologically available.

Compositions whose inert or non-active components (i.e., components other than modafinil) are all liquid at room temperature can be prepared by simply mixing the components without heating. The desired amount of a modafinil compound can be weighed out and dissolved in the mixture of inert components, without heating. Moderate heating, preferably less than 60° C., can be applied to hasten complete mixing of the inert components, to hasten dissolution of a modafinil compound, or both.

Preparation of compositions comprising one or more components that are solid at room temperature is carried out at a moderately elevated temperature, preferably less than 60° C. While moderate heating can be useful, excessive heating can cause decomposition of one or more components of the formulation. For example, decomposition of Polysorbate 80 can occur at temperatures above 60° C. Decomposition of Polysorbate 80 may occur if maintained at 90° C. for more than one hour. As will be appreciated by one of ordinary skill in the art, any deleterious effects of heat accumulate with time. Therefore, when heat is applied, time and temperature will typically be balanced against one another.

The materials, methods, and examples presented herein are intended to be illustrative, and not to be construed as limiting the scope or content of the invention. Unless otherwise defined, all technical and scientific terms are intended to have their art-recognized meanings.

EXAMPLES

A. Materials:

All the materials in the following examples are commercially available or can be readily prepared by one skilled in the art by known or readily available literature methods. The surfactants were used as supplied with no additional purification or dilution. Solvents of USP/NF grade or better were employed.

B. Methods:

1. HPLC

The following HPLC method was used to measure modafinil content in the compositions: A 10 mL serum bottle or 4 mL screw cap vial containing the surfactant solution saturated with modafinil was filtered through a 1.2 µm syringe filter as indicated in the sample preparations described hereinafter. 10 µl of the clear solution was diluted to 1 mL with 990 µL of dimethylsulfoxide (Fischer Certified ACS grade). 10 µL of the diluted solution was used for each injection in the HPLC analysis for modafinil content in each mixture. The column conditions are listed below.

Flow rate: 1.2 mL/min.
Column: ODS, 4.6×20 mm, Column Temp: 30° C.
Mobil phase: 80%(65% Acetonitrile/35%1M phosphate buffer) 20% water
Analysis time: 5 minutes
Wavelength: 222 nanometers Concentration was calculated by comparison to area from a modafinil standard used at 0.4 mg/mL with appropriate dilution. The results are shown in Example 8, Table 1. Each measurement of concentration was an average of two injections.

2. $H_2O$ Dispersion

To determine if a formulation would be suitable as a SEDDS, a 1:20 dilution of each test formulation was prepared with water and timed for the formation of a cloudiness or appearance of a precipitate. In most cases, the failure of the SEEDS was noted by observing a coarse emulsion (as evidenced by cloudiness) or obvious solid particle precipitation within about 10 minutes of mixing.

3. Method for Measurements of Blood Level in Rats Given Modafinil Formulations 21 adult male Sprague-Dawley rats (body weight: 359±6 grams) were fasted overnight prior to use. Each oral formulation was administered via oral gavage (n=3/formulation). The dose of modafinil administered was 100 mg/kg using a dose volume of 3.3 ml/kg. Blood was collected from the lateral tail vein at 0.25, 0.5, 1, 2, 4 and 6 hours post dose. The blood was collected on wet ice and spun at 13,000 RPM for 10 minutes. The supernatant (plasma) was collected and frozen on dry ice. Samples were stored at −70° C. until analysis. The blood serum levels of modafinil in these experiments were measured by LC/MS, as shown in Example 9, Table 2.

Example 1

Preparation of 90% PEG 400, 5% Span® 20, 5% Capmul® MCM (w:w:w)

To 90 grams of PEG 400 were added 5 grams of Span® 20 and 5 grams of Capmul® MCM with stirring until the solution was homogeneous. To a separate container were added 0.1 gram of modafinil and 1 mL of the mixed solvent/surfactant with stirring and heating to 55-60° C. The solution was allowed to cool to room temperature and any undissolved solid was removed by filtering the solution using a 1.2 µL syringe filter.

Example 2

Preparation of 90% PEG 400, 5% Span® 20, 5% lmwitor® 308 (w:w:w)

A quantity of solid Imwitor® 308 was melted and 5 grams were added to 90 grams of PEG-400 and 5 grams of Span® 20 with stirring until the solution was homogenous. To a separate container were added 0.1 gram of modafinil and 1 mL of the mixed solvent/surfactant with stirring and heating to 55-60° C. The solution was allowed to cool to room temperature. Since this mixture is semi-solid, gentle warming to about 35-40° C. was necessary before viscosity was low enough to allow filtration to remove any undissolved modafinil by filtering the solution using a 1.2 µL syringe filter.

Example 3

Preparation of 90% PEG 400, 5% Span® 20, 5% Myrj®-52 (w:w:w)

A quantity of solid Myrj®-52 was melted and 5 grams were added to 90 grams of PEG-400 and 5 grams of Span® 20 with stirring until the solution was homogenous. To a separate container were added 0.1 gram of modafinil and 1 mL of the mixed solvent/surfactant with stirring and heating to 55-60° C. The solution was allowed to cool to room temperature. Since this mixture is semi-solid, gentle warming to about 35-40° C. was necessary before viscosity was low enough to allow filtration to remove any undissolved modafinil by filtering the solution using a 1.2 µL syringe filter.

Example 4

Preparation of 70% PEG 400, 15% Tween® 80, 15% Labrasol® (w:w:w)

To 70 grams of PEG-400 were added 15 grams of Tween® 80 (Polysorbate 80) and 15 grams of Labrasol® with stirring until the solution was homogeneous. To a separate container were added 0.1 gram of modafinil was weighed and 1 mL of the mixed solvent/surfactant with stirring and heating to 55-60° C. The solution was allowed to cool to room temperature and any undissolved solid was removed by filtering the solution using a 1.2 µL syringe filter.

Example 5

Preparation of 70% PEG 400, 15% Tween® 80, 15% Myrj®-52 (w:w:w)

A quantity of solid Myrj®-52 was melted and 15 grams were added to 70 grams of PEG-400 and 15 grams of Tween® 80 with stirring until the solution was homogenous. To a separate container were added 0.1 gram of modafinil and 1 mL of the mixed solvent/surfactant with stirring and heating to 55-60° C. The solution was allowed to cool to room temperature. Since this mixture is semi-solid, gentle warming to about 35-40° C. was necessary before viscosity was low enough to allow filtration to remove any undissolved modafinil by filtering the solution using a 1.2 µL syringe filter.

Example 6

Preparation of 70% PEG 400, 15% Tween® 80, 15% Capmul® MCM (w:w:w)

To 70 grams of PEG-400 were added 15 grams of Tween®80 (Polysorbate 80) and 15 grams of Capmul® MCM with stirring until the solution was homogeneous. To a separate container were added 0.1 gram of modafinil and 1 mL of the mixed solvent/surfactant with stirring and heating to 55-60° C. The solution was allowed to cool to room temperature and any undissolved solid was removed by filtering the solution using a 1.2 µL syringe filter.

Example 7

Preparation of 70% PEG 400 15% Tween® 80, 15% Imwitor® 308 (w:w:w)

A quantity of solid Imwitor®-308 was melted and 15 grams were added to 70 grams of PEG-400 and 15 grams of Tween® 80 with stirring until the solution was homogenous. To a separate container were added 0.1 gram of modafinil and 1 mL of the mixed solvent/surfactant with stirring and heating to 55-60° C. The solution was allowed to cool to room temperature. Since this mixture is semi-solid, gentle warming to about 35-40° C. was necessary before viscosity was low enough to allow filtration to remove any undissolved modafinil by filtering the solution using a 1.2 µL syringe filter.

Example 8

Solubility of Modafinil in Particle-forming Compositions

The solubility of modafinil in the compositions of Examples 1-7, as measured by HPLC, is shown below in Table 1.

TABLE 1

Solubility of Modafinil in Particle-forming Compositions

| | Excipients (w:w:w) | | | Solubility (mg/ml) |
|---|---|---|---|---|
| Ex. 1 | 90% PEG 400 | 5% Span 20 | 5% Capmul ® MCM | 50 |
| Ex. 2 | 90% PEG 400 | 5% Span 20 | 5% Imwitor ® 308 | 52 |
| Ex. 3 | 90% PEG 400 | 5% Span 20 | 5% Myrj ® 52 | 57 |
| Ex. 4 | 70% PEG 400 | 15% Tween ™ 80 | 15% Labrasol ® | 43 |
| Ex. 5 | 70% PEG 400 | 15% Tween ™ 80 | 15% Myrj ® 52 | 47 |
| Ex. 6 | 70% PEG 400 | 15% Tween ™ 80 | 15% Capmul ® MCM | 40 |
| Ex. 7 | 70% PEG 400 | 15% Tween ™ 80 | 15% Imwitor ® 308 | 44 |

Example 9

Blood Serum Levels of Modafinil in Rats

The blood serum levels of modafinil in rats, upon administration of compositions of Examples 1-7, is shown below in Table 2. The Oraplus® composition is intended to mimic the bioavailability of solid modafinil dosed in an oral fashion such as a tablet, but without the difficulty of administering a tablet to the rat. Oraplus® is an oral suspending vehicle that is commercially available (Paddock Laboratories, Minneapolis, Minn.), and is primarily composed of purified water, microcrystalline cellulose, sodium carboxymethylcellulose, xanthan gum, carrageenan, citric acid and sodium phosphate (as buffers), simethicone (antifoaming agent), and potassium sorbate and methyl paraben (preservatives).

TABLE 2

Blood Serum Levels of Modafinil in Rats

| Modafinil Solutions | BLOOD SERUM LEVEL (ng/ml) | | | | | | |
|---|---|---|---|---|---|---|---|
| TIME (Hrs.) | Ex. 1 | Ex. 2 | Ex. 3 | Ex. 4 | Ex. 5 | Ex. 6 | Oraplus |
| 0.25 | 2.6 | 11.2 | 2.6 | 2.2 | 0.5 | 1.0 | 3.4 |
| 0.5 | 2.2 | 5.1 | 4.2 | 2.3 | 9.7 | 3.4 | 4.9 |
| 1 | 2.3 | 16.5 | 3.8 | 1.4 | 8.2 | 1.7 | 3.0 |
| 2 | 1.2 | 1.7 | 2.8 | 0.6 | 5.8 | 3.4 | 1.9 |
| 4 | 0.6 | 1.4 | 0.7 | 0.6 | 3.5 | 1.9 | 0.4 |
| 6 | 0.4 | 0.4 | 0.2 | 0.3 | 0.2 | 0.4 | 0.2 |

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

What is claimed is:

1. A non-aqueous liquid solution comprising a modafinil compound, at least one organic solvent selected from the group consisting of glycerin, propylene glycol, diethylene glycol ethyl ether, propylene carbonate, tetraglycol, a medium chain length monoglyceride, and polyethylene glycol, and at least one surfactant, characterized in that the solution spontaneously forms an aqueous, liquid, homogeneous, stable composition of non-crystalline particles when contacted with an aqueous medium.

2. The solution of claim 1, wherein the modafinil compound is modafinil.

3. The solution of claim 2, wherein modafinil is present in the solution at a concentration of about 1 to about 500 mg/ml.

4. The solution of claim 3, wherein modafinil is present in the solution at a concentration of about 1 to about 200 mg/ml.

5. The solution of claim 4, wherein modafinil is present in the solution at a concentration of about 20 to about 80 mg/ml.

6. The solution of claim 2, wherein upon administration of the solution to a subject in need thereof modafinil has a blood serum level of about 0.05 to about 30 µg/ml in said subject.

7. The solution of claim 6, wherein the blood serum level is from about 1 to about 20 µg/ml.

8. The solution of claim 1, wherein the solution is pharmaceutically acceptable.

9. The solution of claim 1, wherein the surfactant or surfactants comprise from about 0.5% to about 50% (w/w) of the solution.

10. The solution of claim 9, wherein the surfactant or surfactants comprise from about 1% to about 20% (w/w) of the solution.

11. The solution of claim 1, wherein the surfactant or surfactants is a polyoxyethylene sorbitan fatty acid ester, a polyethylene glycol ether, a saturated polyglycolized glyceride, a fatty acid ester of polyethylene glycol, a medium chain monoglyceride, a medium chain fatty acid ester, d-α-tocopheryl polyethylene glycol succinate, a polyethylene/propylene glycol copolymer, block copolymers of ethylene oxide and propylene oxide, a polyoxyl stearate, an ethoxylated castor oil, or an ethoxylated hydroxystearic acid.

12. The solution of claim 11, comprising a first surfactant and a second surfactant.

13. The solution of claim 12, wherein the second surfactant is a polyoxyethylene sorbitan fatty acid ester.

14. The solution of claim 13, wherein the second surfactant is sorbitan monolaurate or Polysorbate 80.

15. The solution of claim 11, wherein the solution comprises Polysorbate 80, glyceryl caprylate/caprate and a mixture of glyceryl tricaprate and glyceryl tricaprilate.

16. The solution of claim 1, further comprising benzyl alcohol, α-phenethyl alcohol or β-phenethyl alcohol.

17. The solution of claim 1, wherein the solution comprises a modafinil compound at a concentration of about 1 to about 100 mg/ml; a first surfactant selected from a polyoxyethylene sorbitan fatty acid ester, a polyethylene glycol ether, a saturated polyglycolized glyceride, a fatty acid ester of a polyethylene glycol, a medium chain monoglyceride, a medium chain fatty acid ester, d-α-tocopheryl polyethylene glycol succinate, a polyethylene/propylene glycol copolymer, block copolymers of ethylene oxide and propylene oxide, a polyoxyl stearate, an ethoxylated castor oil, and an ethoxylated hydroxystearic acid; a second surfactant selected from a polyoxyethylene sorbitan fatty acid ester; and an organic solvent selected from glycerin, propylene glycol, diethylene glycol ethyl ether, propylene carbonate, tetraglycol, a medium chain length monoglyceride, and a polyethylene glycol.

18. The solution of claim 17, wherein the modafinil compound is modafinil.

19. The solution of claim 18, wherein the first surfactant is a saturated polyglycolized glyceride, a fatty acid ester of a polyethylene glycol, or a medium chain monoglyceride; the second surfactant is a polyoxyethylene sorbitan fatty acid ester; and the organic solvent is a polyethylene glycol.

20. The solution of claim 19, wherein the first surfactant is glyceryl caprylate/caprate, glyceryl monocaprylate or polyethoxylated (40) stearic acid; the second surfactant is sorbitan monolaurate; and the organic solvent is PEG-300 or PEG-400.

21. The solution of claim 20, wherein the solution comprises 90% PEG-400, 5% sorbitan monolaurate, 5% glyceryl caprylate/caprate (w/w/w).

22. The solution of claim 20, wherein the solution comprises 90% PEG-400, 5% sorbitan monolaurate, 5% glyceryl monocaprylate (w/w/w).

23. The solution of claim 20, wherein the solution comprises 90% PEG-400, 5% sorbitan monolaurate, 5% polyethoxylated (40) stearic acid (w/w/w).

24. The solution of claim 19, wherein the first surfactant is glyceryl caprylate/caprate, glyceryl monocaprylate, polyethoxylated (40) stearic acid or a mixture of polyoxyethylene glyceryl caprylate and polyoxyethylene glyceryl caproate; the second surfactant is polyoxyethylene (80) sorbitan monooleate;and the organic solvent is PEG-300 or PEG-400.

25. The solution of claim 24, wherein the solution comprises 70% PEG-400, 15% polyoxyethylene (80) sorbitan monooleate, 15% glyceryl caprylate/caprate (w/w/w).

26. The solution of claim 24, wherein the solution comprises 70% PEG-400, 15% polyoxyethylene (80) sorbitan monooleate, 15% glyceryl monocaprylate (w/w/w).

27. The solution of claim 24, wherein the solution comprises 70% PEG-400, 15% polyoxyethylene (80) sorbitan monooleate, 15% polyethoxylated (40) stearic acid (w/w/w).

28. The solution of claim 24, wherein the solution comprises 70% PEG-400, 15% polyoxyethylene (80) sorbitan monooleate, 15% of a mixture of polyoxyethylene glyceryl caprylate and polyoxyethylene glyceryl caproate (w/w/w).

29. The solution of claim 17, wherein the modafinil compound is the levorotatory form of modafinil.

30. The solution of claim 1, comprising one or more unit doses of a modafinil compound.

31. The solution of claim 30, comprising one unit dose of a modafinil compound.

32. The solution of claim 31, wherein the unit dose comprises 200 mg of a modafinil compound.

33. The solution of claim 31, wherein the unit dose comprises 100 mg of a modafinil compound.

34. The solution of claim 1, wherein the solution is suitable for oral administration to a subject.

35. The solution of claim 34, wherein the solution is encapsulated within a capsule.

36. The solution of claim 35, wherein the capsule is a soft gelatin capsule.

37. The solution of claim 35, wherein the capsule is a hard capsule.

38. The solution of claim 1, wherein the modafinil compound is the levorotatory form of modafinil.

39. The solution of claim 1, wherein the organic solvent has an average molecular weight of about 1500 daltons or less.

40. A method of treating a disease or disorder in a subject, comprising administering to a subject a therapeutically effective amount of a non-aqueous liquid solution comprising a modafinil compound, at least one organic solvent selected from the group consisting of glycerin, propylene glycol, diethylene glycol ethyl ether, propylene carbonate, tetraglycol, a medium chain length monoglyceride, and polyethylene glycol, and at least one surfactant, wherein the solution is characterized by the fact that it spontaneously forms an aqueous, liquid, homogeneous, stable composition of non-crystalline particles when contacted with an aqueous medium, and wherein the disease or disorder is selected from the groups consisting of sleepiness, tiredness, Parkinson's disease, cerebral ischemia, stroke, sleep apneas, eating disorders, attention deficit hyperactivity disorder, cognitive dysfunction or fatigue; or for the promotion of wakefulness, stimulation of appetite, or stimulation of weight gain.

41. The method of claim 40, wherein the modafinil compound is modafinil.

42. The method of claim 40, wherein the modafinil compound is the levorotatory form of modafinil.

43. A method of treating a disease or disorder in a subject, comprising:
 (a) preparing a non-aqueous liquid solution comprising a modafinil compound, at least one organic solvent selected from the group consisting of glycerin, propylene glycol, diethylene glycol ethyl ether, propylene carbonate, tetraglycol, a medium chain length monoglyceride, and polyethylene glycol, and at least one surfactant;
 (b) contacting the non-aqueous solution with an aqueous medium to spontaneously form an aqueous, liquid, homogeneous, stable composition of non-crystalline particles; and
 (c) administering a therapeutically effective amount of the aqueous, liquid, homogeneous, stable composition of non-crystalline particles to a subject;
 wherein the disease or disorder is selected from the group consisting of sleepiness, tiredness, Parkinson's disease, cerebral ischemia, stroke, sleep apneas, eating disorders, attention deficit hyperactivity disorder, cognitive dysfunction or fatigue; or for the promotion of wakefulness, stimulation of appetite, or stimulation of weight gain.

44. The method of claim 43, wherein the modafinil compound is modafinil.

45. The method of claim 43, wherein the modafinil compound is the levorotatory form of modafinil.

* * * * *